US00PP32626P3

(12) United States Plant Patent
Kerley et al.

(10) Patent No.: US PP32,626 P3
(45) Date of Patent: Dec. 15, 2020

(54) ***CALENDULA* PLANT NAMED 'KERCALDIVIMP'**

(50) Latin Name: *Calendula hybrida*
Varietal Denomination: Kercaldivimp

(71) Applicants: Timothy Edward Kerley, Willingham (GB); Sarah Elisabeth Kerley, Willingham (GB); David William Kerley, Over (GB); Priscilla Grace Kerley, Over (GB)

(72) Inventors: Timothy Edward Kerley, Willingham (GB); Sarah Elisabeth Kerley, Willingham (GB); David William Kerley, Over (GB); Priscilla Grace Kerley, Over (GB)

( * ) Notice: Subject to any disclaimer, the term of this patent is extended or adjusted under 35 U.S.C. 154(b) by 0 days.

(21) Appl. No.: 16/873,421

(22) Filed: Apr. 9, 2020

(65) Prior Publication Data

US 2020/0329602 P1 Oct. 15, 2020

(30) Foreign Application Priority Data

Apr. 10, 2019 (CA) ..... PBR 19-9751

(51) Int. Cl.
*A01H 6/14* (2018.01)
*A01H 5/02* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14
See application file for complete search history.

*Primary Examiner* — Annette H Para
(74) *Attorney, Agent, or Firm* — C. A. Whealy

(57) ABSTRACT

A new and distinct cultivar of *Calendula* plant named 'Kercaldivimp', characterized by its upright to outwardly spreading and uniformly mounding plant habit; moderately vigorous growth habit; freely branching habit; freely and continuously flowering habit; long flowering period; large fully double inflorescences with bright orange-colored ray florets; good container and landscape performance and tolerance to Powdery Mildew.

2 Drawing Sheets

Figure 1:
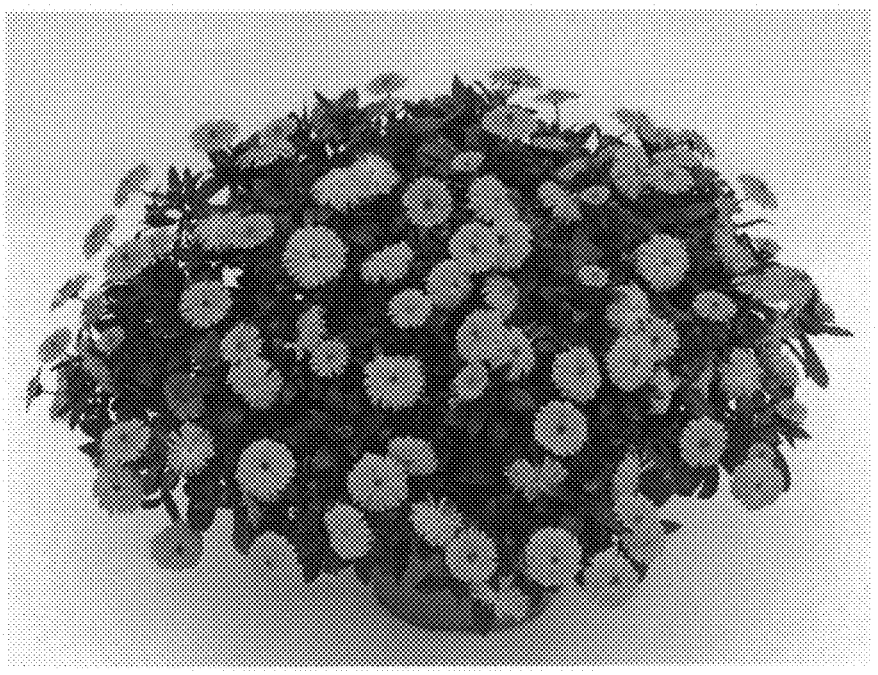

Botanical designation: *Calendula hybrida.*
Cultivar denomination: 'KERCALDIVIMP'.

CROSS-REFERENCE TO A RELATED APPLICATION AND STATEMENT REGARDING PRIOR DISCLOSURES BY INVENTORS/APPLICANTS

This application claims priority to a Canadian Plant Breeders' Rights application filed on Apr. 10, 2019, application number 19-9751. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Calendula* plant, botanically known as *Calendula hybrida* and hereinafter referred to by the name 'Kercaldivimp'.

The new *Calendula* plant is a product of a planned breeding program conducted by the Inventors in Cambridge, United Kingdom. The objective of the breeding program is to create new uniformly mounding *Calendula* plants that flower continuously for a long period of time and have good container and landscape performance.

The new *Calendula* plant originated from a cross-pollination in May, 2015 of a proprietary selection of *Calendula hybrida* identified as code number 13-22-19, not patented, as the female, or seed, parent with *Calendula hybrida* 'Kercalsun', disclosed in U.S. Plant Pat. No. 29,994, as the male, or pollen, parent. The new *Calendula* plant was discovered and selected by the Inventors as a single flowering plant from within the progeny of the stated cross-pollination in a controlled greenhouse environment in Cambridge, United Kingdom in July, 2016.

Asexual reproduction of the new *Calendula* plant by vegetative tip cuttings in a controlled greenhouse environment in Cambridge, United Kingdom since August, 2016 has shown that the unique features of this new *Calendula* plant are stable and reproduced true to type in successive generations.

SUMMARY OF THE INVENTION

Plants of the new *Calendula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Calendula*. These characteristics in combination distinguish 'Kercaldivimp' as a new and distinct *Calendula* plant:

1. Upright to outwardly spreading and uniformly mounding plant habit.
2. Moderately vigorous growth habit.
3. Freely branching habit.
4. Freely and continuously flowering habit.
5. Long flowering period.
6. Large fully double inflorescences with bright orange-colored ray florets.
7. Good container and landscape performance and tolerance to Powdery Mildew.

Plants of the new *Calendula* differ primarily from plants of the female parent selection in the following characteristics:

1. Plants of the new *Calendula* are more outwardly spreading than and not as upright as plants of the female parent selection.
2. Plants of the new *Calendula* have double inflorescences whereas plants of the female parent selection have semi-double inflorescences.
3. Plants of the new *Calendula* have shorter peduncles than plants of the female parent selection.
4. Plants of the new *Calendula* have not been observed to set seed whereas plants of the female parent selection have abundant seed set.
5. Plants of the new *Calendula* are more tolerant to Powdery Mildew than plants of the female parent selection.

Plants of the new *Calendula* differ primarily from plants of the male parent, 'Kercalsun', in ray floret color as plants of the new *Calendula* have bright yellow-colored ray florets whereas plants of 'Kercalsun' have bright yellow-colored ray florets.

Plants of the new *Calendula* can be compared to plants of *Calendula hybrida* 'Kercaldiva', disclosed in U.S. Plant Pat. No. 30,517. In side-by-side comparisons, plants of the new *Calendula* differ primarily from plants of 'Kercaldiva' in the following characteristics:

1. Plants of the new *Calendula* are more outwardly spreading than and not as upright as plants of 'Kercaldiva'.
2. Inflorescences of plants of the new *Calendula* are more fully double than inflorescences of plants of 'Kercaldiva'.
3. Plants of the new *Calendula* have not been observed to set seed whereas plants of 'Kercaldiva' have abundant seed set.
4. Plants of the new *Calendula* are more tolerant to Powdery Mildew than plants of 'Kercaldiva'.

Plants of the new *Calendula* also can be compared to plants of *Calendula hybrida* 'Winter Wonders Orange & Ice', not patented. In side-by-side comparisons, plants of the new *Calendula* differ primarily from plants of 'Winter Wonders Orange & Ice' in the following characteristics:

1. Plants of the new *Calendula* are more freely branching than plants of 'Winter Wonders Orange & Ice'.
2. Plants of the new *Calendula* are more freely flowering than plants of 'Winter Wonders Orange & Ice'.
3. Plants of the new *Calendula* have not been observed to set seed whereas plants of 'Winter Wonders Orange & Ice' have abundant seed set.
4. Plants of the new *Calendula* are more tolerant to Powdery Mildew than plants of 'Winter Wonders Orange & Ice'.

BRIEF DESCRIPTION OF THE PHOTOGRAPHS

The accompanying photographs illustrate the overall appearance of the new *Calendula* plant showing the colors as true as it is reasonably possible to obtain in colored reproductions of this type. Colors in the photographs may differ slightly from the color values cited in the detailed botanical description which accurately describe the colors of the new *Calendula* plant.

The photograph on the first sheet (FIG. 1 of 2) is a side perspective view of a typical flowering plant of 'Kercaldivimp' grown in a container.

Figure 2:
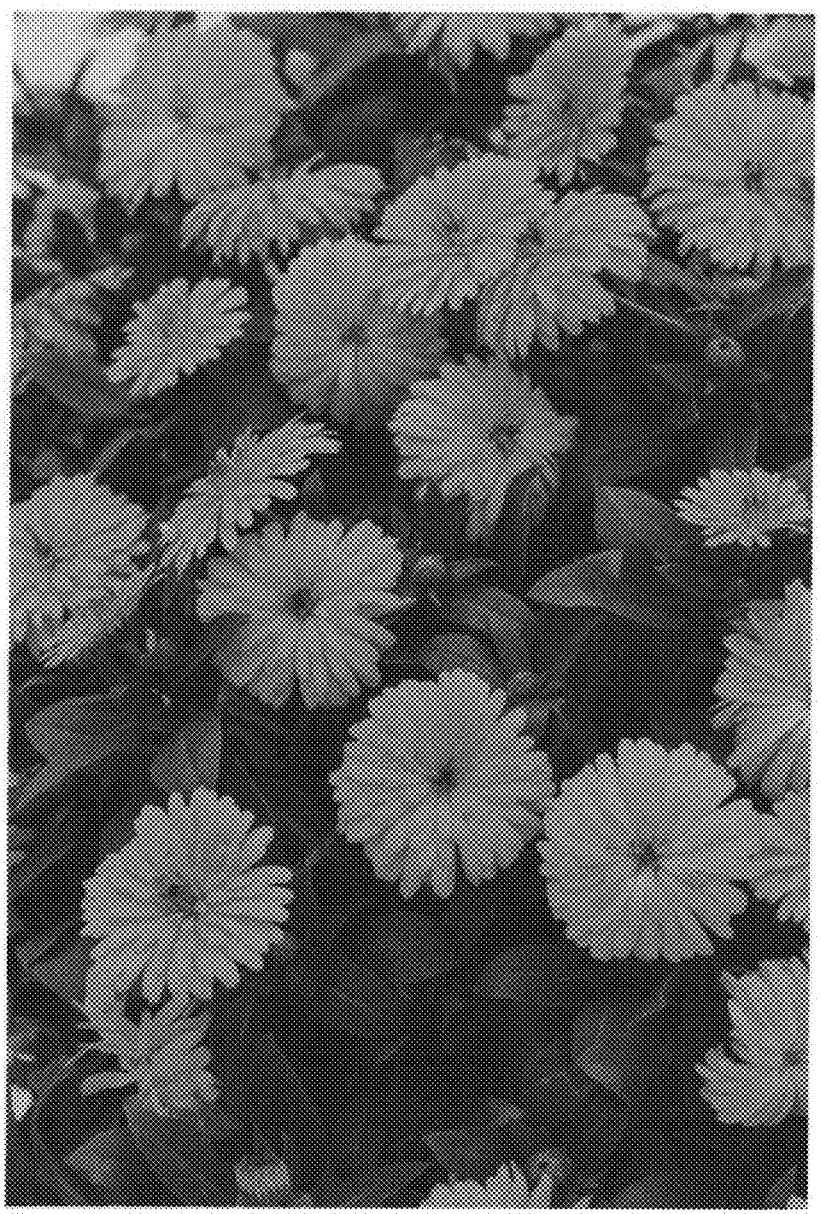

The photograph on the second sheet (FIG. 2 of 2) is a close-up view of a typical flowering plant of 'Kercaldivimp'.

DETAILED BOTANICAL DESCRIPTION

The aforementioned photographs and following observations and measurements describe plants grown during the spring in 7.5-liter containers in a glass-covered greenhouse in Cambridge, United Kingdom and under cultural practices typical of commercial *Calendula* production. Plants were twelve weeks from planting rooted cuttings when the photographs and description were taken. In the following description, color references are made to The Royal Horticultural Society Colour Chart, 2015 Edition, except where general terms of ordinary dictionary significance are used.

Botanical classification: *Calendula hybrida* 'Kercaldivimp'.

Parentage:

*Female, or seed, parent*.—Proprietary selection of *Calendula hybrida* identified as code number 13-22-19, not patented.

*Male, or pollen, parent*.—*Calendula hybrida* 'Kercalsun', disclosed in U.S. Plant Pat. No. 29,994.

Propagation:

*Type*.—By vegetative tip cuttings.

*Time to initiate roots, summer*.—About seven days at soil temperatures about 21° C.

*Time to initiate roots, winter*.—About ten days at soil temperatures about 21° C.

*Time to produce a rooted young plant, summer*.—About three weeks at soil temperatures about 21° C.

*Time to produce a rooted young plant, winter*.—About four weeks at soil temperatures about 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright to somewhat outwardly spreading and uniformly mounding plant habit; moderately vigorous growth habit and moderate growth rate.

*Branching habit*.—Freely branching habit with about five to six primary stems each with about four to six secondary lateral branches; dense and bushy appearance.

*Plant height*.—About 31 cm.

*Plant diameter or spread*.—About 49 cm.

*Lateral branches*.—Length: About 31 cm. Diameter: About 8 mm. Internode length: About 2.5 cm. Strength: Strong. Aspect: Main stems, mostly upright; lateral stems about outwardly from main stems. Texture and luster: Sparsely pubescent, ridged; matte. Color: Close to 144B and 144A.

Leaf description:

*Arrangement*.—Alternate, simple; sessile.

*Length*.—About 9 cm.

*Width*.—About 3.6 cm.

*Shape*.—Oblanceolate.

*Apex*.—Acute.

*Base*.—Truncate.

*Margin*.—Entire.

*Texture and luster, upper and lower surfaces*.—Sparsely pubescent; matte.

*Venation pattern*.—Pinnate.

*Color*.—Developing leaves, upper surface: Close to 147A. Developing leaves, lower surface: Close to 147B. Fully expanded leaves, upper surface: Close to 146A; venation, close to 146B. Fully expanded leaves, lower surface: Close to 146B; venation, close to 146C.

Inflorescence description:

*Appearance*.—Double-type inflorescences developing on terminal and axillary peduncles; inflorescences with numerous ray florets; disc floret development has not been observed; inflorescences positioned on strong peduncles; inflorescences face mostly upright to outwardly.

*Flowering habit*.—Freely flowering habit with 52 to 63 inflorescences per plant at one time.

*Fragrance*.—None detected.

*Flowering response*.—Early flowering habit, plants begin flowering about eight weeks after planting in Cambridge, United Kingdom.

*Natural flowering season*.—Long flowering period, plants flower continuously from spring until frost in temperate regions; in Cambridge, United Kingdom, plants flower from March until November.

*Inflorescence longevity*.—Depending on actual temperature, inflorescences last about ten to eleven days on the plant; inflorescences persistent.

*Inflorescence buds*.—Height: About 1.2 cm. Diameter: About 1.3 cm. Shape: Ovoid. Texture and luster: Pubescent; matte. Color: Close to 137C; ray florets, close to 163B and apices, close to 165A.

*Inflorescence diameter*.—About 5.7 cm.

*Inflorescence height* (*depth*).—About 1.8 cm.

*Receptacle diameter*.—About 6 mm.

*Receptacle height*.—About 3 mm.

*Receptacle color*.—Close to 145B.

*Ray florets*.—Number of ray florets per inflorescence: About 101 arranged in about four to six whorls. Length: About 2.6 cm. Width: About 5 mm. Shape: Oblanceolate. Apex: Acute or fimbriate with three points. Base: Narrowly cuneate. Margin: Entire. Aspect: Mostly horizontal, apices reflexing with development. Texture and luster, upper surface: Smooth, glabrous; glossy. Texture and luster, lower surface: Mostly smooth and glabrous, proximally, pubescent; matte. Color: When opening, upper surface: Brighter than N25C to N25D; at the apices, slightly tinged with close to 165A; towards the base, close to brighter than 14B. When opening, lower surface: Close to 14A; at the apices, slightly tinged with close to 165A; towards the base, close to 12A. Fully opened, upper surface: Close to N25C; towards the base, close to 6A; venation, similar to lamina; color does not change with development. Fully opened, lower surface: Close to N25D; at the apices, slightly tinged with close to 165A; towards the base, close to 9B; venation, similar to lamina or close to 166C; color does not change with development.

*Disc florets*.—To date, disc floret initiation and development have not been observed on inflorescences of plants of the new *Calendula*.

*Phyllaries*.—Quantity per inflorescence and arrangement: About 26 arranged in a single whorl. Length: About 1.1 cm. Width: About 2 mm. Shape: Oblanceolate. Apex: Acute. Base: Truncate. Margin: Entire. Aspect: When opening, mostly upright; open inflorescences, mostly horizontal. Texture and luster, upper surface: Smooth, glabrous; slightly glossy. Texture and luster, lower surface: Pubescent; matte. Color, upper surface: Close to 147A. Color, lower surface: Close to 147B.

*Peduncles*.—Length, terminal peduncle: About 3.4 cm. Diameter, terminal peduncle: About 2 mm. Strength: Strong. Aspect: Mostly upright. Texture and luster: Slightly ridged, pubescent; slightly glossy. Color: Close to 146B.

*Reproductive organs*.—Androecium: Not observed on ray florets. Gynoecium: Quantity per ray floret: One. Pistil length: About 9 mm. Style length: About 5 mm. Style color: Proximally, close to 1D and distally, close to 1B. Stigma shape: Bi-parted. Stigma color: Close to 168A. Ovary color: Close to 145C to 145D.

*Seeds and fruits*.—To date, seed and fruit development have not been observed on plants of the new *Calendula*.

Pathogen & pest resistance: Plants of the new *Calendula* have been observed to be tolerant to Powdery Mildew (*Golovinomyces cichoracearum*). Plants of the new *Calendula* have not been shown to be resistant to pests and other pathogens common to *Calendula* plants.

Garden performance: Plants of the new *Calendula* have been observed to have good garden performance and to tolerate temperatures from about −5° C. to about 30° C.

It is claimed:

1. A new and distinct *Calendula* plant named 'Kercaldi-vimp' as illustrated and described.

* * * * *